US006695765B1

(12) United States Patent
Beebe et al.

(10) Patent No.: US 6,695,765 B1
(45) Date of Patent: Feb. 24, 2004

(54) MICROFLUIDIC CHANNEL EMBRYO AND/ OR OOCYTE HANDLING, ANALYSIS AND BIOLOGICAL EVALUATION

(75) Inventors: David J. Beebe, Monona, WI (US); Ian K. Glasgow, Madison, WI (US); Matthew B. Wheeler, Tolono, IL (US); Henry Zeringue, Madison, WI (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/570,483

(22) Filed: May 12, 2000

Related U.S. Application Data

(63) Continuation-in-part of application No. 09/289,137, filed on Apr. 8, 1999, now Pat. No. 6,193,647.

(51) Int. Cl.[7] .............................. A61B 17/43; A61D 7/00
(52) U.S. Cl. ........................................................ 600/33
(58) Field of Search ....................... 600/33, 35; 435/7.2

(56) References Cited

U.S. PATENT DOCUMENTS

| | | | |
|---|---|---|---|
| 4,676,274 A | 6/1987 | Brown | 137/806 |
| 4,832,759 A | 5/1989 | Curtis et al. | 435/285 |
| 5,296,375 A | 3/1994 | Kricka et al. | 435/291 |
| 5,304,487 A | 4/1994 | Wilding et al. | 435/291 |
| 5,376,252 A | 12/1994 | Ekstrom et al. | 204/299 |
| 5,427,946 A | 6/1995 | Kricka et al. | 435/291 |
| 5,486,335 A | 1/1996 | Wilding et al. | 422/55 |
| 5,498,392 A | 3/1996 | Wilding et al. | 422/68.1 |
| 5,512,476 A | 4/1996 | Gordon | 435/240.26 |
| 5,635,358 A | 6/1997 | Wilding et al. | 435/7.2 |
| 5,637,469 A | 6/1997 | Wilding et al. | 435/7.21 |
| 5,691,194 A | 11/1997 | Gordon | 435/287.1 |
| 5,744,366 A | 4/1998 | Kricka et al. | 436/63 |
| 5,757,482 A | 5/1998 | Fuchs et al. | 356/246 |
| 5,779,868 A | 7/1998 | Parce et al. | 204/604 |
| 5,989,835 A | 11/1999 | Dunlay et al. | 435/7.2 |
| 6,193,647 B1 * | 2/2001 | Beebe et al. | 600/33 |

FOREIGN PATENT DOCUMENTS

| | | |
|---|---|---|
| WO | 9115750 | 10/1991 |
| WO | 9322053 | 11/1993 |
| WO | 9322055 | 11/1993 |
| WO | 9747390 | 12/1997 |

OTHER PUBLICATIONS

J.M. Lim, B.C. Reggio, R.A. Godke, W. Hansel, "A Continuous Flow, Perifusion Culture System for 8– to 16–Cell Bovine Embryos Derived from In Vitro Culture", *Theriogenology*, vol. 46, pp. 1441–1450, 1996.

J.A. Pruitt, D.W. Forrest, R.C. Burghardt, J.W. Evans, D.C. Kraemer, "Viability and Ultrastructure of Equine Embryos Following Culture in a Static or Dynamic System", *Journal of Reproduction and Fertility*, vol. 44 (Supp.), pp. 405–410, 1991.

C.L. Keefer, S.L. Stice, A.M. Paprocki, P. Golueke, "In vitro Culture of Bovine IVM–IVF Embryos: Cooperative Interaction Among Embryos and the Role of Growth Factors", *Theriogenology*, vol. 41, pp. 1323–1331, 1994.

(List continued on next page.)

*Primary Examiner*—Kevin Shaver
*Assistant Examiner*—Brian Szmal
(74) *Attorney, Agent, or Firm*—Greer, Burns & Crain, Ltd.

(57) ABSTRACT

Microfluidic embryo scaled channels for handling and positioning embryos provide the opportunity to evaluate and treat embryos in improved manners Fluid flow is used to move and position embryos within microfluidic channels and channel geometries may be used to place embryos at specific locations. Surface properties and compliance (deformation) properties of embryos are evaluated as a predictor of viability. The microfluidic channels provide the opportunity for fine controls of pressure to conduct various evaluations at forces slightly below which damage to embryos is known to occur.

13 Claims, 9 Drawing Sheets

OTHER PUBLICATIONS

P.C.H. Li and D.J. Harrison, "Transport, Manipulation, and Reaction of Biological Cells On–Chip Using Electrokinetic Effects", *Analytical Chemistry*, vol. 69, No. 8, pp. 1564–1568, 1997.

S.J. Choi, I. Glasgow, H. Zeringue, D.J. Beebe, M.B. Wheeler, "Development of Microelectromechanical Systems to Analyze Individual Mammalian Embryos: Embryo Biocompatibility", *Biol. Reprod.*, vol. 58 (Suppl. 1), p. 96 (abstr.), 1998.

K. Chun, G. Hashiguchi, H. Toshiyoshi, H. Fujita, "An Array of Hollow Microcapillaries for the Controlled Injection of Genetic Materials into Animal/Plant Cells", presented at *Technical Digest of Twelfth IEEE International Conference on Micro Electro Mechanical Systems (MEMS '99)*, Orlando, FL, 1999, pp. 406–411.

I.K. Glasgow, H.C. Zeringue, D.J. Beebe, S.J. Choi, J.T. Lyman, M.B. Wheeler, "Individual Embryo Transport and Retention on a Chip for a Total Analysis System", presented at the Solid–State Sensor and Actuator Workshop, Hilton Head Island, SC, 1998.

I.K. Glasgow, H.C. Zeringue, D.J. Beebe, S.J. Choi, J.T. Lyman, M.B. Wheeler, "Individual Embryo Transport and Retention on a Chip", in Micro Total Analysis Systems '98; Proceedings of the TAS '98 Workshop held in Banff, Canada, D.J. Harrison and A. van den Berg, Eds. Boston: Kluwer Academic Publishers, pp. 199–202, 1998.

M.B. Wheeler, S.J. Choi, I.K. Glasgow, H.C. Zeringue, J.T. Lyman, D.J. Beebe, "Development of Microelectromechanical Systems to Analyze Individual Mammalian Embryos: Embryo Biocompatibility and Individual Embryo Transport on Silicon A Chip", *Arquivos da Faculdade de Veterinaria UFRGS*, Sociedade Brasileira de Transferencia de Embraoes, vol. 26, No. 1, 1998 (Supl), p. 391.

K. Hosokawa, T. Fujii, I. Endo, "Hydrophobic Microcapillary Vent for Pneumatic Manipulation of Liquid in $\mu$TAS", in Micro Total Analysis Systems '98; Proceedings of the TAS '98 Workshop held in Banff, Canada, D.J. Harrison and A. van den Berg, Eds. Boston: Kluwer Academic Publishers, pp. 307–310, 1998.

"Microchip Arrays put DNA on the Spot", *Science*, vol. 282, Oct. 16, 1998, pp. 396–405.

M. Lane and D.K. Gardner, "Selection of Viable Mouse Blastocysts Prior to Transfer using a Metabolic Criterion", *Human Reproduction*, vol. 21, No. 9, 1996, pp. 1975–1978.

* cited by examiner

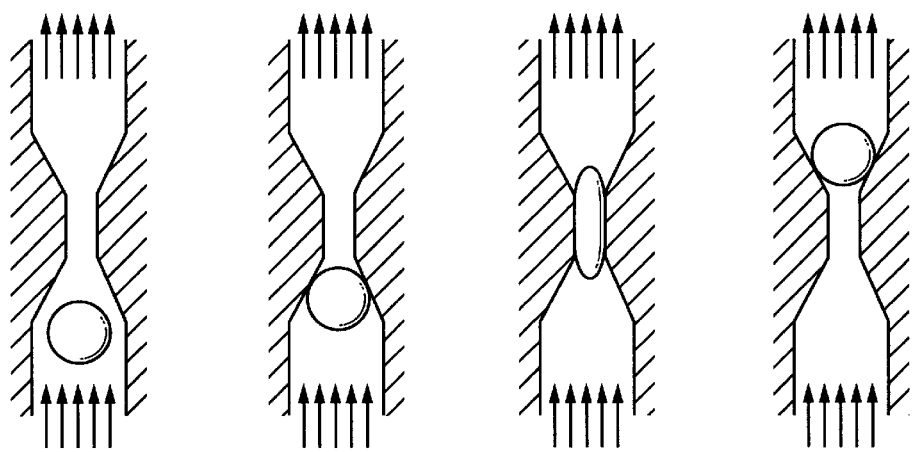
FIG. 9(a)  FIG. 9(b)  FIG. 9(c)  FIG. 9(d)
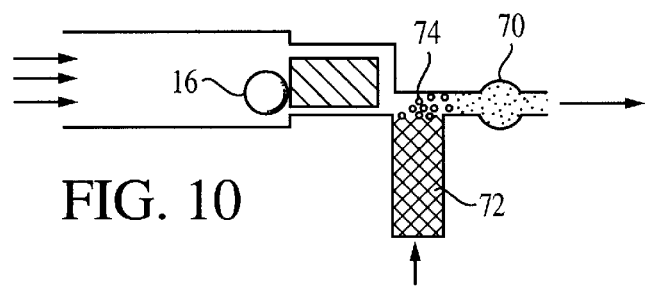
FIG. 10
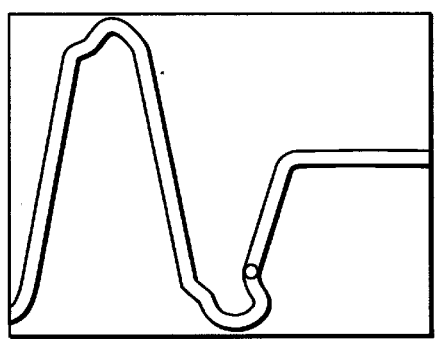 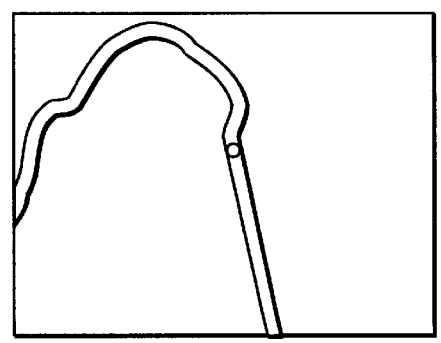
FIG. 7(a)  FIG. 7(b)

MICROFLUIDIC CHANNEL EMBRYO AND/ OR OOCYTE HANDLING, ANALYSIS AND BIOLOGICAL EVALUATION

REFERENCE TO RELATED APPLICATION

This application is a continuation-in-part of, and claims priority under 35 USC §120 from U.S. application Ser. No. 09/289,137 filed Apr. 4–8, 1999, now U.S. Pat. No. 6,193,647.

FIELD OF THE INVENTION

The present invention generally concerns handling of embryos. The invention also concerns handling of oocytes (prefertilized embryos), and eggs. Embryo, as used herein, therefore encompasses oocytes, and eggs as well as fertilized embryos. The invention more specifically concerns microfluidic handling of embryos for culturing, manipulation, and analysis.

BACKGROUND OF THE INVENTION

Technology assisted reproduction techniques in which embryos are handled independently from their mammalian biological source are growing in importance and frequency of use. Such techniques have great direct benefit to persons unable to have babies through unassisted sexual reproduction. The agricultural industries also increasingly rely upon such assisted reproduction techniques. Embryo manipulation is used in livestock reproduction to control such things as the faster genetic evolution of cattle and permitting the genetic characteristics of a single exceptional cow or bull to be passed on to far greater numbers of offspring than would be possible through unassisted sexual reproduction.

Livestock embryo manipulation is becoming more routine due to the development of gene manipulation, cloning, and in vitro fertilization (IVF) techniques. The overall goal of embryo manipulation in livestock is to increase production efficiency, especially with regard to reproduction, milk production or production of specific milk components, lean tissue growth with reduced fat content and decreased susceptibility to specific diseases. Embryo transfer is also used to introduce or rescue valuable germplasm and propagate rare breeding animals such as endangered exotic species.

Expense and relatively low success rates place significant burdens on the use of these assisted reproduction techniques for humans as well as livestock. In human reproduction such expense and failure adds emotional as well as economic burdens. In addition, safeguards against failures often result in unwanted or unmanageable multiple births, as well as additional stored embryos which require maintenance and additional difficult decision making at some later point in time. Expense is the primary concern in livestock reproduction.

Failure rates in reproduction techniques as well as testing and other embryo handling techniques are attributable primarily to the significant handling and manipulation of embryos in executing these techniques. Animal reproductive technologies have advanced in recent years, but the physical tools used in animal reproduction have not changed significantly. Fine-bore glass pipets are still one of the basic tools of the embryologist. Using standard petri dishes, procedures such as in vitro maturation of eggs (IVM), in vitro fertilization, and embryo culture (EC) require picking up and placing individual eggs and embryos several times for each procedure.

Such handling and movement from one petri dish to another provides significant potential for damage or contamination. Perhaps more important, though, is the failure of a stationary embryo in a petri dish to simulate the corresponding natural biological reproduction condition. Some efforts have been made to move embryos in petri dishes via agitation of the dish, but this is a haphazard approach. Expense is also created here due to the relatively large amount of biological medium required for the manual petri dish conventional embryo handling methods. Bovine embryos are individually handled with pipets and large, expensive manipulators. Large quantities of biological medium including growth agents for human embryo culturing renders the corresponding in vitro procedure even more expensive. Livestock growth factors, for example, have costs exceeding $200 per 50 µg.

Such static culture systems also fail to allow for changing the milieu in the culture medium as the embryo develops. Current culture systems with flowing medium have culture chambers as small as 0.2 to 0.5 ml. However, the culture volumes are greater than needed and medium is replenished too quickly. The endogenous growth factors that enhance development are diluted out and washed away. The large volumes of medium required substantially increase costs when expensive growth factors, such as IGF-II ($200 per 50 µg) are used. In addition, known systems cannot track individual embryos.

Conventional handling techniques also provide limited ability to evaluate embryos. An ability to evaluate pre-implantation embryos, including embryos, pronuclear zygotes, and oocytes, would provide a better success rate for implantations. Currently, the morphology of most embryos is evaluated prior to their transfer into a recipient. Morphology examination will sort out embryos with gross defects but is not a highly reliable indicator of viability. Chemical monitoring over a period of time has been used, but requires numerous measurements over a period of time. The result is a much better predictor of viability, on the order of 80%, but many embryos fail to survive the monitoring process. This requires use of additional embryos. This results in multiple births, other complications, and entails additional labor costs.

Conventional techniques also provide harsh methods for removal of the zona pellucida, which is a critical step in the making of chimeric embryos. Conventionally, an embryo is mouth pipetted from one tissue culture dish containing the culture media, into a culture dish containing an acidic media. The embryo is left in the media for a period of time (tens of seconds) then mouth pipetted into a dish containing fresh culture media. The embryo is then flushed in and out of the pipette a few times to quickly disperse all of the acidic media and minimize damage to the cell membranes. The opening of the mouth pipette is about the same size as the embryo, and the flushing therefore causes sheer stresses on the embryos. The imprecision of mouth pipetting therefore provides ample opportunity for damage.

Thus, there is a need for an improved embryo handling device and method which addresses problems in known embryo handling techniques. An improved embryo handling device and method should provide for an improved simulation of natural conditions. It should also provide a building block upon which larger and/or more powerful and accurate instruments may be based, such as embryo culturing systems, embryo analysis systems, embryo storage systems, and similar systems. There is a further need for improved evaluation of embryo viability.

SUMMARY OF THE INVENTION

These needs are met or exceeded by the present microfluidic embryo handling device and method. The invention simulates biological rotating of embryos. An embryo fluidic channel moves an embryo inserted therein with fluid, and is sized on the same scale as the particular type of embryo or embryos to be handled. The sizing and fluid communication produces a simulated biological rotating of embryos. In addition, the fluid flow with and around the embryo or embryos prevents stagnation, reducing the likelihood of the embryo or embryos developing injuries that may be analogous to "bed sores".

The invention also permits the biological medium fluid to be altered gradually, having significant advantages compared to repeatedly manually transferring an embryo from one medium to another medium in a pipet or petri dish. Gradual changes avoid the shock from sudden changes in local environment. The microfluidic system of the invention further permits the co-culturing of an embryo with other embryos, co-culturing of an embryo or embryos with cells upstream of the embryo(s), and maintenance of a separate control culture that shares a common biological medium with a subject embryo(s) thereby ensuring that test embryos see the same environmental conditions as the subject embryo(s).

Other aspects of the invention concern specific uses of the broader principles of microfluidic embryo handling to manipulate, evaluate and position embryos. One aspect concerns the use of a gradual series of constrictions to remove surrounding material from an embryo. This has been demonstrated to remove surrounding cumulus from oocyte. A first few constrictions cut the cumulus, which can then be sucked off of the oocyte in a final small constriction which is sized to prevent passage of the oocyte.

Embryo evaluation is also realized in accordance with the basic invention principles. In a preferred evaluation, surface properties and compliance (deformation) properties of embryos are evaluated. The microfluidic channels provide the opportunity for fine controls of pressure to conduct various evaluations at forces slightly below which damage to embryos is known to occur. Measurement of the distance and/or speed which embryos roll in a same pressure gradient microfluidic channel provides information, with healthy embryos traveling slower or a shorter distance as they demonstrate more stiction to channel walls. Positioned at a constriction, healthy embryos also appear to deform less than unhealthy embryos that are more readily pulled into a constriction. In addition, healthy embryos appear to resume their shape better.

Fluid from microfluidic channels is easily collected downstream without altering the embryo environment, providing a better opportunity for chemical analysis of fluid chemical analysis than convention manual handling and sampling techniques. In addition, all of the fluid collected from a microfluidic channel has passed over the embryo. This provides better evaluation information than fluids stagnant around an embryo in a Petri dish. Through the invention, medium can continuously or periodically pass over embryos and be collected downstream, eliminating additional handling required in a petri dish technique. The invention provides more consistent fluid samples since fluid can be repeatedly collected in the same manner, whereas samples taken from petri dishes may vary based upon placement of the pipette that suctions medium, i.e., how far or how close to an embryo.

Use of clear channel sections allows for many types of optical analysis. Stains or dyes may be added for visual inspection at clear sections. Clear sections also provide the opportunity to use image analysis devices, since the microfluidic channels may be configured to precisely position an embryo at a location for analysis by imaging equipment.

Precise position of embryos using channels and constrictions of the invention, and/or flow manipulation, further enables an improved method for zona pellucida removal of mammalian embryos. Embryos are moved through flow to a precise location where lysing agent can be washed over the embryo to achieve zona removal.

BRIEF DESCRIPTION OF THE DRAWINGS

Other objects, features and advantages of the invention will be apparent to artisans who read the detailed description and reference the accompanying drawings, of which:

FIGS. 7(a) and 7(b) illustrate portions of constricted channel useful for cumulus removal from oocytes;

FIGS. 9(a)–9(d) illustrate a deformation evaluation of an embryo used as an indicator of embryo viability; and FIG. 10 illustrates a preferred microfluidic channel configuration for fluid analysis or sampling in accordance with the invention.

DETAILED DESCRIPTION OF THE INVENTION

The present invention provides a microfluidic embryo handling device which reduces stress to embryos handled outside their natural biological host. The device and method reproduce simulated biological rotating of an embryo through fluid assisted movement in a channel that encourages embryo slipping and rotating. Rotating, as used herein, may include complete rotation or partial rotation. Partial rotation might also be referred to as a rocking motion.

Figure 1:
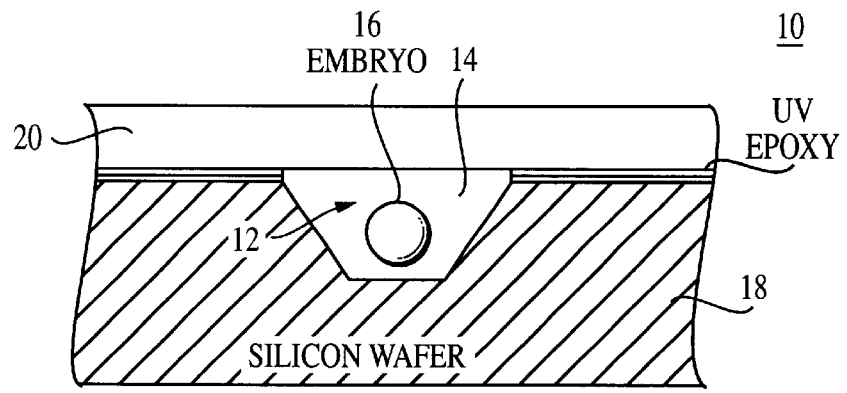
FIG. 1 shows a cross section of a preferred microfluidic embryo handling device constructed in accordance with the present invention.

Referring now to FIG. 1 shown is a cross-section of a microfluidic embryo handling device 10 including a embryo transport network 12 formed at least in part by a generally embryo scale channel 14. An embryo 16 in the channel 14 will move with fluid flow in the channel 14, while the close dimensions of the channel cause the embryo 14 to move with a simulated biological rotating motion. Channels up to ten times the embryo size have been used to create rolling and slipping. In biological hosts, developing embryos in their initial stages of development move toward the uterus to which they will attach with a rotating and slipping motion. The microfluidic channel 14 produces a simulation of such motion.

Sizing of a channel is important to establish the biological rotating. Height is the critical dimension, and it has been found that heights up to about three times the diameter of an embryo induce the rotating. This ratio may be determined to vary somewhat because fluid flow also plays a role, but the three to one maximum ratio has been found to produce the rotating. It will be appreciated that the channel width is less important. The width may be selected arbitrarily. Thus, if embryos are to be kept in single order, then the width would be less than twice the embryo diameter. If more embryos are desired, larger width channels may be used.

Networks of the channels 14 provide a means to culture embryos, as well as to move and place embryos to desired locations. During its initial stages of development, the size of most mammalian embryos remain generally constant during the first few days after fertilization. Thus, the size of the channels 14 provide no impediment to culturing an embryo therein. Advantageously, the embryo 16 may be kept moving and/or may have a continuous or pulsed fluid flow passed around it to avoid potential detrimental biological effects on the embryo 16.

A preferred exemplary construction of a device 10 including a channel is also illustrated in FIG. 1. The microfluidic channel 14 may be formed by any suitable micromachining technique into a suitable material, such as a silicon wafer 18. The material chosen must be capable of being sterilized and should not pose a biological threat to embryos. The channel (s) 14 of the device are sealed through a cover 20. Forming the cover of glass or other transparent material allows convenient visual monitoring of embryos in channel(s) 14. A bonding agent 22 bonds the cover 20 to the wafer 18. Additionally, the material of the cover could be formulated to shield harmful radiation from the embryo(s) in channel(s) 14.

Unlike other cells that tend to float in a fluid medium, the relatively large and heavy embryos sink to the bottom of the microfluidic channels 14. Typical mammalian preimplantation embryos of interest are 90 to 180 $\mu$m diameter spheres. In each embryo, a membrane surrounds each cell (blastomere) and the zona pellucida, a glycoprotein membrane or shell, surrounds the entire cell mass. The cells divide several times during the first few days after fertilization, the volume of the embryo remains constant and an egg may be fertilized and cultured to a blastocyst in the same device constructed based upon the principles of the invention. The blastocyst is the final stage before an embryo implants in the uterus.

Also important to production of such a device and similar devices is the ability to handle individual embryos, or small numbers of embryos. Positioning embryos to given locations, moving to alternate locations, and maintaining constant or changing biological conditions around the embryo(s) are abilities provided by basic principles of the present invention, and permit the construction of fertilization, culturing, testing, and other devices which rely on some or all of those abilities. For continuous movement of an embryo through a culture period of time, long channels may be created, or a loop may be formed. Alternately, a parking of an embryo may occur at a culturing station like those shown in FIGS. 6(a) and 6(b). A compartment or channel of limited size may also be used to roll an embryo back and forth therein by changing fluid flow, as will be further discussed with respect to FIGS. 6(a) and 6(b).

Figure 2A:
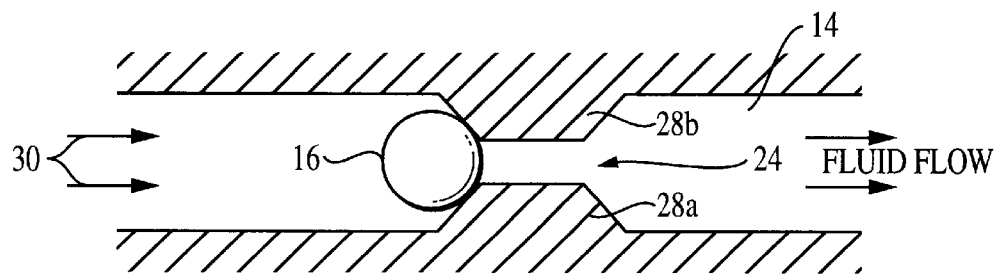
FIG. 2(a) is a top view showing a preferred narrow microfluidic channel constriction for embryo positioning.
Figure 2B:
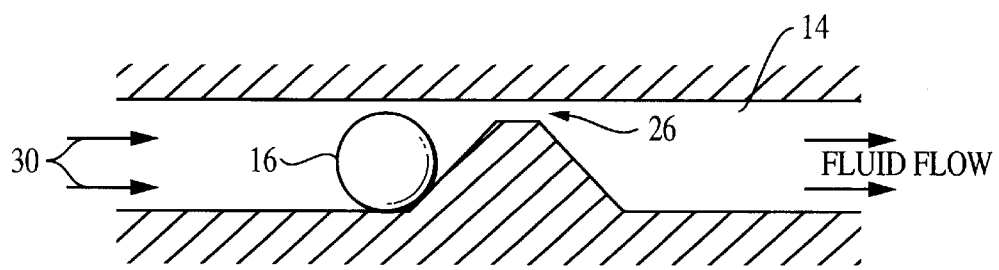
FIG. 2(b) is a cross-sectional view of an alternate preferred shallow microfluidic channel constriction for embryo positioning.

Accurate positioning of individual embryos is provided by the invention through the use of constrictions, preferred examples of which are shown in FIGS. 2(a) and 2(b). FIG. 2(a) is a top view of a cross section of a narrow constriction 24 formed in a microfluidic channel 14. There are many reasons such an accurate positioning may be desirable in an embryo handling device 10. Analysis instruments built into the device may require an embryo to be precisely positioned at electrodes, a photodetector, the focal point of a microscope, or other similar sensing device. Transporting an embryo to the constriction 24 permits such required positioning without resort to feedback systems. An embryo 16 is freed from the constriction 24 simply by reversing the flow of biological fluid medium 30. Even when held at the constriction, an embryo 16 experiences a flow of biological fluid medium around it since fluid 30 will flow past it and through the constriction 24. This is advantageous since an embryo in stagnant fluid has an increased potential to develop "bed sores", a suspected but yet unproven explanation for low success rates in embryo handling technology.

Sidewall portions 28a, 28b of the microfluidic channel 14 constrict it at a desired location to prevent passage of an embryo 16 therethrough. The constriction 24 does not completely close the microfluidic channel 14 so that fluid biological medium 30 may pass an embryo 16 positioned at the constriction 24. FIG. 2(b) shows a side cross-section of an alternate shallow constriction 26 where the fluid biological medium 30 is similarly able to pass when an embryo 16 is positioned at the constriction. Other shapes of constriction are also possible. Generally, any shape which prevents passage of an embryo 16 while simultaneously allowing fluid flow through the constriction, e.g., asymmetric shapes and comb-like fibers, is acceptable to position embryos in a device 10 according to the invention. It is preferred that the constriction be sized such that positioning of an embryo prevents the embryo from passing without an increased pressure from the fluid pressure used in a device 10 to move embryos. Constriction length should also be kept small enough to avoid fluid control problems since the constriction portion of a microfluidic channel will have much higher fluidic resistance per unit length than unrestricted portions of the microfluidic channels 14.

Figure 2C:
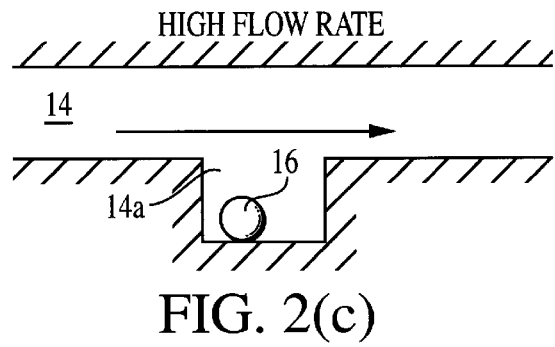
FIGS. 2(c) and 2(d) are schematic views of an alternate preferred fluid dynamic constriction.
Figure 2D:
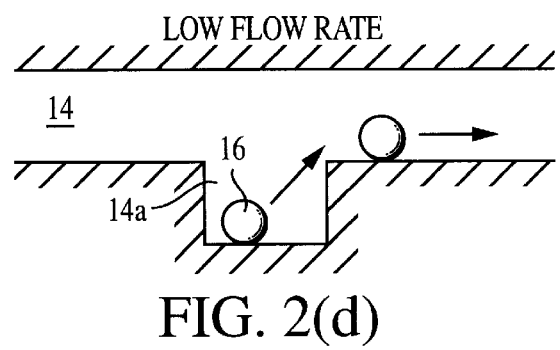
Figure 2E:
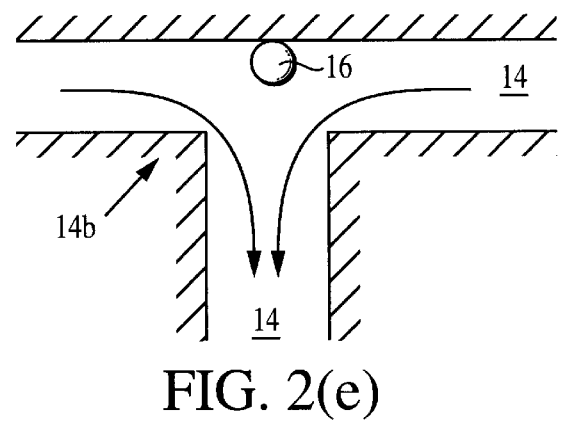
FIG. 2(e) is a schematic view of an alternate preferred fluid dynamic constriction.
Figure 2F:
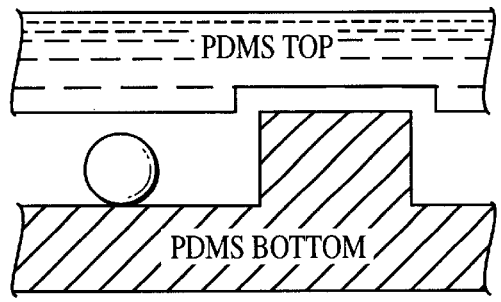
FIG. 2(f) illustrates an alternate preferred mechanical constriction geometry.
Figure 2G:
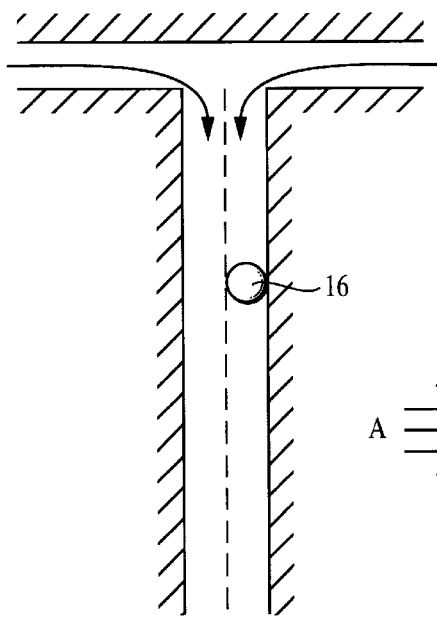
FIG. 2(g) shows a particular flow pattern in the FIG. 2(e) fluid dynamic constriction useful, for example, for zona treatment.
Figure 2H:
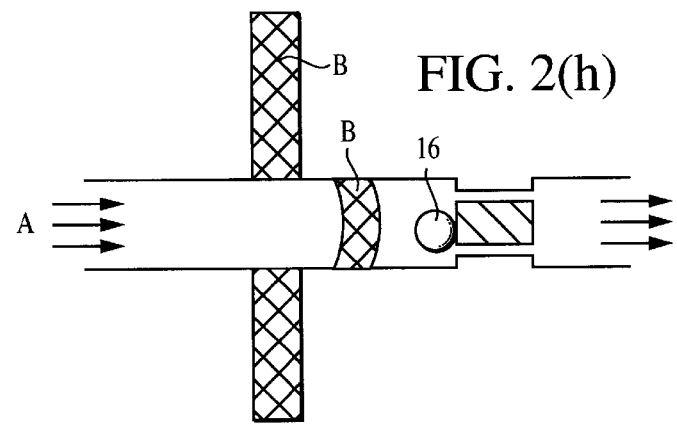
FIG. 2(h) shows another flow pattern useful for delivering a discrete fluid to an embryo.

Fluid dynamics within microfluidic channels 14 may also be used to position embryos. Whereas the constrictions of FIGS. 2(a) and 2(b) are physical constrictions, an effective fluid dynamic constriction is realized in FIGS. 2(c) and 2(d) without a physical barrier to passage of an embryo. In FIGS. 2(c) and 2(d), an increased depth microfluidic channel well portion 14a defines a position where an embryo 16 may be intentionally held by control of fluid dynamics, i.e., the flow over and through the well portion 14a. In FIG. 2(c) high laminar or nonlaminar flows will cause an embryo 16 to stay in the well portion because flow separation occurs at the leading edge of the well portion 14*a*. During (lower) flow rates, the fluid stream lines follow the contour of the microfluidic channel 14, including the well portion 14*a*, to sweep an embryo out of the well portion. Predetermined flow rates to respectively hold and sweep out an embryo can be calculated for particular well geometries and sizings, or may be determined experimentally. FIG. 2(*e*) shows an alternate strategy for positioning an embryo 16. In FIG. 2(*e*), a T-junction 14*b* is formed at the intersection of microfluidic channels 14. In a balanced fluid flow condition, as illustrated in FIG. 2(*e*), there will be no flow at the embryo's position, permitting it to remain in position. Though none is illustrated, an indent or other small physical shape might enhance stability of the embryo 16 in FIG. 2(*e*). Another constriction geometry is shown in FIG. 2(*f*).

With the geometries and flows of FIGS. 2(*a*)–2(*f*) it is possible to position an embryo at a precise location within a network of microfluidic channels. This affords an opportunity for visual inspection, embryo removal, embryo testing, analysis of the embryo by imaging or other devices and treatment of an embryo. Many mechanical manipulations of the embryo can accordingly be effected, and any treatment, analysis, or manipulation that would benefit from such accurate positioning an moving of the embryos, and the ability to manipulate and control the flow environment therefore benefits from application of the invention.

A specific exemplary treatment technique using constrictions and microfluidic channel flows to position an embryo in a device like the FIGS. 2(*a*)–2(*e*) devices is zona pellucida removal from an embryo. The zona pellucida is a glycoprotein matrix surrounding embryonic cells. A chimera, a single animal with two DNA sets, is made by removing the zona pellucida and bringing the separate embryonic cells together. Zona thinning or removal is also important to transgenic procedures, IVF, and cell biopsy. A parking location is defined for zona removal, see, e.g., FIG. 2(*f*). The low aspect ratio, on the order of 0.01, for the top section of constriction in FIG. 2(*f*) may require support to avoid collapse. In a prototype device, this was achieved with small PDMS (polydimethylsiloxane) posts surrounding the constriction region. The constriction region against which an embryo, or multiple embryos, will rest may be shaped to bring embryos together as will be necessary for chimera formation. A v-shaped resting surface will bring embryos together in such a fashion. Upstream of a constriction like that shown in FIG. 2(*f*), microfluidic channels are configured such that a controlled wash of acidic solution can be caused to flow a parked embryo or embryos. For example, an acidic inlet can t-junction into a main flow leading to the parking area of FIG. 2(*f*). A lysing plug, for example, provides acidic solution into the main channel near and upstream of the constriction for a short period to achieve zona removal. With the microfluidic channels, precise control of the flow is achieved for a required period of time. In a prototype device, syringe connections to a main microfluidic channel including the constriction and a "T" intersection channel were used to control embryo positioning and flows over positioned embryos. Syringes offer precise control of fluid, and computer controlled microsyringes will add precision to flow control and timing.

An alternate mechanical method of removing a zona involves mechanical damage to the zona. This is achieved, for example, by passing the zona through a microfluidic channel of the invention including a mechanical structure to nick or cut the zona. The precise fluid control of the invention also creates the possibility of a laminar flow method to "nick" a zona. In the "T" junction of FIG. 2(*e*) two separate flows of two different solutions meet at the "T" and flow into a single channel, as shown in FIG. 2(*g*), where a dotted line indicates separation of flow. These flows may be kept separate in the single channel by laminar flow. One flow (on the left) contains, for example, acid for zona thinning. Driving pressures control the lateral position of the interface between the two solutions such that the zona of an embryo 16 is "nicked" by the acid.

Figure 2I:
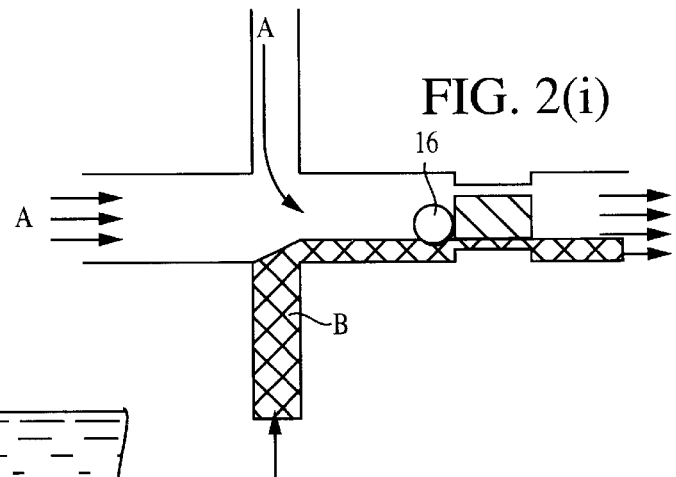
FIG. 2(I) shows another flow pattern useful for delivering a discrete fluid to an embryo.

The method for delivering discrete fluid to an embryo for zona removal is also applicable to discrete delivery of other fluids, for example, spermatozoa. Alternate multiple flow arrangements are shown in FIGS. 2(*h*) and 2(I) where a cross junction of microfluidic channels is shown. In FIG. 2(*h*), a main fluid flow A is controlled to prevent entry of fluid B except for a limited time to form a plug of the B fluid. A plug of fluid B is formed through fluid control, i.e., a burst of increased pressure in the B flow, or a temporary reduction or stop in the A flow. A created plug of fluid B then flows with flow A over the embryo 16. Sizing of the channels used to deliver flow B determines sizing of a plug of fluid B that can be formed. This configuration has been used to deliver an acid for zona removal, but could deliver other fluids in similar fashion. FIG. 2(I) has the same geometric configuration, but uses fluid flow to continuously deliver flow B in a portion of a channel. This is similar to the control in FIG. 2(*g*).

Figure 3B:
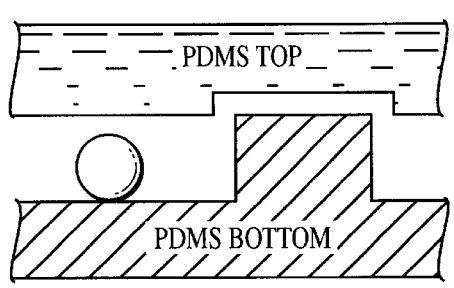
FIG. 3(b) is a schematic cross-section of microfluidic channel for a zona pellucida removal procedure of the invention.

A culture and test device 31 including a constriction like that shown in FIG. 2(*a*) for positioning an embryo is illustrated in FIG. 3(*a*). The device 31 has fluid flow in a network 32 of microfluidic channels 14 driven by gravity based upon levels of fluid 30 in a plurality of fluid reservoirs 34. Any suitable means for driving fluid 30 is contemplated as being compatible with the general principles of the invention, e.g. pumping, but the gravity method illustrated in FIG. 3(*a*) is preferred for its simplicity and efficiency. Directions of flows are controlled simply by levels of fluid in reservoirs 34. Thus, for example, an embryo 16 held at a constriction 24 for culturing or examination by a suitable instrument is positioned by first setting fluid levels to cause its travel from inlet port 36 to constriction 24, and is released when fluid flow is reversed through the constriction 24. Removal of the embryo 16 is accomplished by causing fluid flow to move it to exit port 38.

During movement through the microfluidic channels 14 of the network 32, the embryo(s) roll and slip to simulate natural movement of embryos toward a uterus in a mammalian host, as discussed above. This desirable manner of moving may be aided by a suitable surfactant such as BSA (bovine serum albumin). The surfactant will help to promote some slippage of the embryo as it rolls.

FIG. 3(*a*) also illustrates an additional advantage of the invention, in the provision of a parallel additional microfluidic handling and culturing device 31*a*. The additional device 31*a* has a structure similar to that of device 31, but may have fewer or even a single microfluidic channel. Ideally, the structure is the same. The important feature of the device 31*a* is that it shares a common fluid source with inlet port 36 and outlet port 38 of primary device. Embryo(s) handled in the device 31*a* are isolated biologically from embryo(s) in primary device 31, but experience the same biological conditions through sharing the same fluid source, pressure and/or the same biological medium condition. In an exemplary use, the additional device 31*a* therefore might form an important control culture in which development or lack of development of test embryo(s) could confirm suitability or unsuitability of conditions created in the primary device 31.

Figure 4:
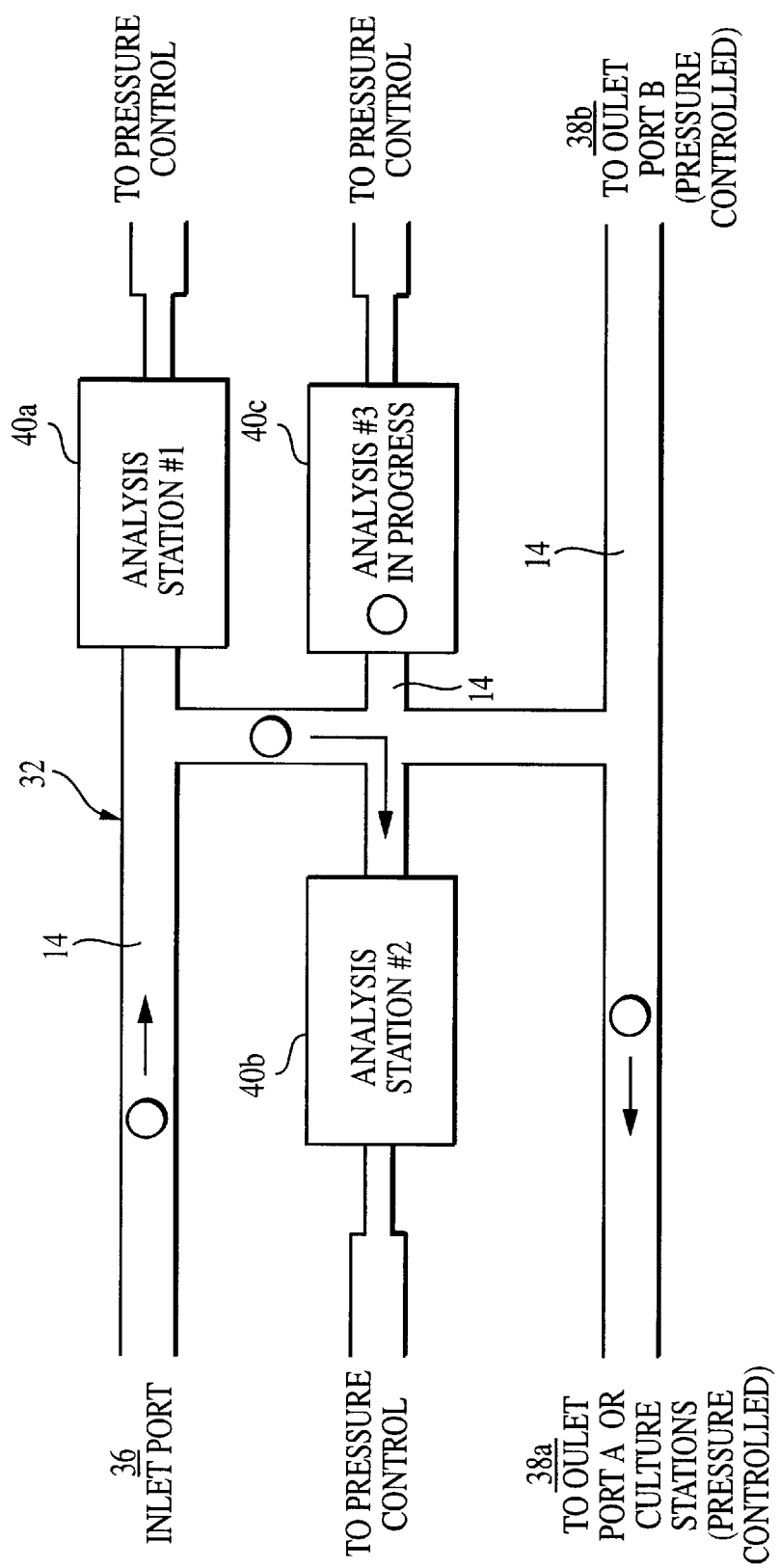
FIG. 4 is a block diagram of an embryo analysis device constructed in accordance with the present invention.

FIG. 4 is a block diagram of an embryo analysis device. In the FIG. 4 device a network 32 of microfluidic channels 14 moves embryos to one or more analysis stations 40a, 40b or 40c. Embryos are positioned at a given analysis station through constrictions like those described above. The analysis stations may include any instrument capable of obtaining information concerning an embryo, with the constriction being formed to position embryos at the proper sensing point for the particular instrument used in an analysis station. Embryos are moved out of the device through one or more exit ports 38a, 38b, which might alternately lead to a culturing station in the form of a parking area for an embryo, an additional length of microfluidic channel 14, or a microfluidic channel loop for continuous movement of an embryo during culturing.

Figure 5A:
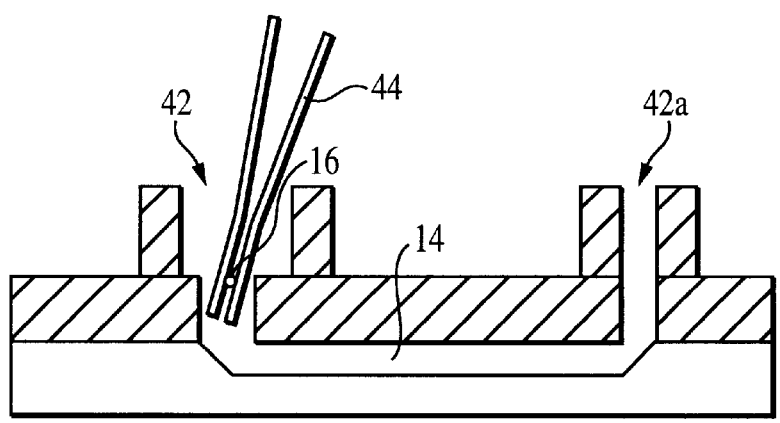
FIGS. 5(a)–5(c) illustrate preferred embryo microfluidic channel insertion and removal structures in accordance with the present invention.
Figure 5B:
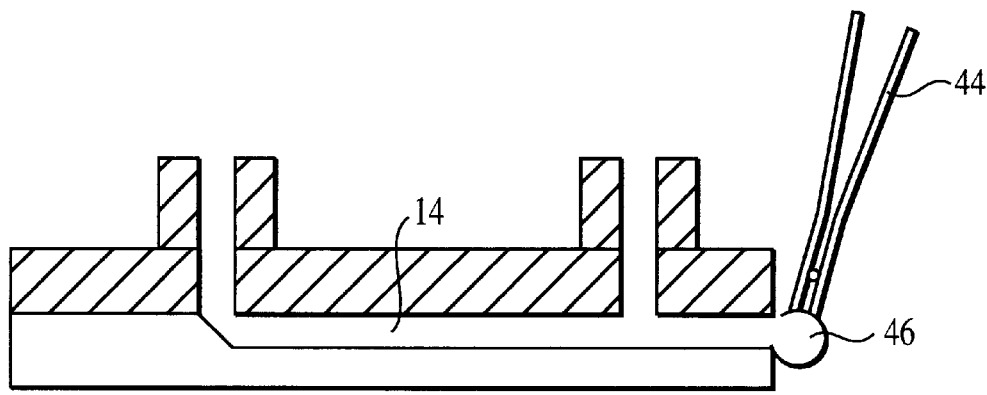
Figure 5C:
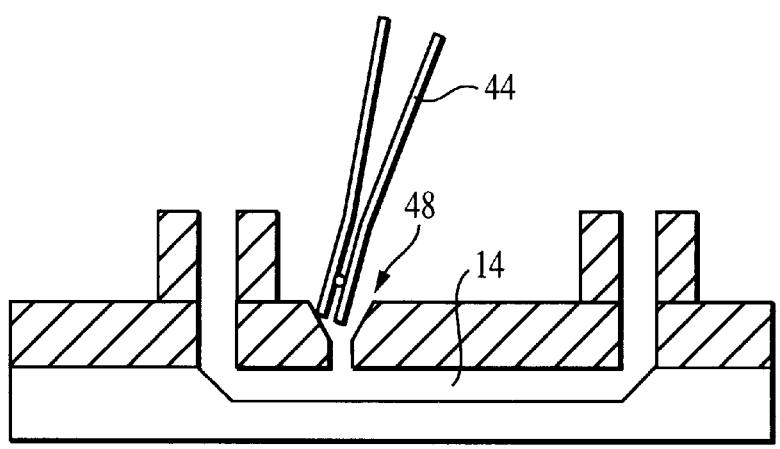

Inlet and outlet ports used in devices of the invention may comprise any conventional manner or structure for embryo insertion or removal. However, additional preferred structures for insertion and removal are shown in FIGS. 5(a)-5(c). In FIG. 5(a), a well 42 which is in fluid communication with a microfluidic channel 14 is used. Fluid in the well 42 preferably also comprises a gravity feed which helps drive microfluidic flow in the channel 14. An embryo 16 is placed in the well 42 and moves into the channel 14 with biological medium, or simply sinks unaided into the channel 14 if no flow condition is created. A second similar well 42 may be used to remove an embryo using a pipet 44 or similar device, which might also be used for insertion. In FIG. 5(b), a hanging drop 46 at the end of a channel 14 is used for insertion and removal. The hanging drop 46 is held by surface tension. After embryo insertion, fluid may be added at that point, or the embryo may be sucked in by fluid flow in the device. Alternately, the device may be inclined to promote embryo movement away from the hanging drop 46. In FIG. 5(c), a funnel shaped hole 48 in direct communication with channel 14 is used for insertion and removal. The funnel shape aids positioning of a pipet 44 or similar device. Surface tension at a small diameter hole 48 will prevent fluid from leaking out, but the pressure in channel 14 must not exceed the point that would defeat surface tension and cause fluid to leak out. Inserted embryos will sink into the channel 14, while removal may be accomplished by drawing fluid from hole 48 when an embryo approaches. Of course, any of the FIG. 5 techniques may be combined with each other or conventional techniques for insertion and removal in a given handling device. In addition, the wells 42 or holes 48 may be covered by a removable cover or flap as protection against contamination and/or evaporation.

Figure 6A:
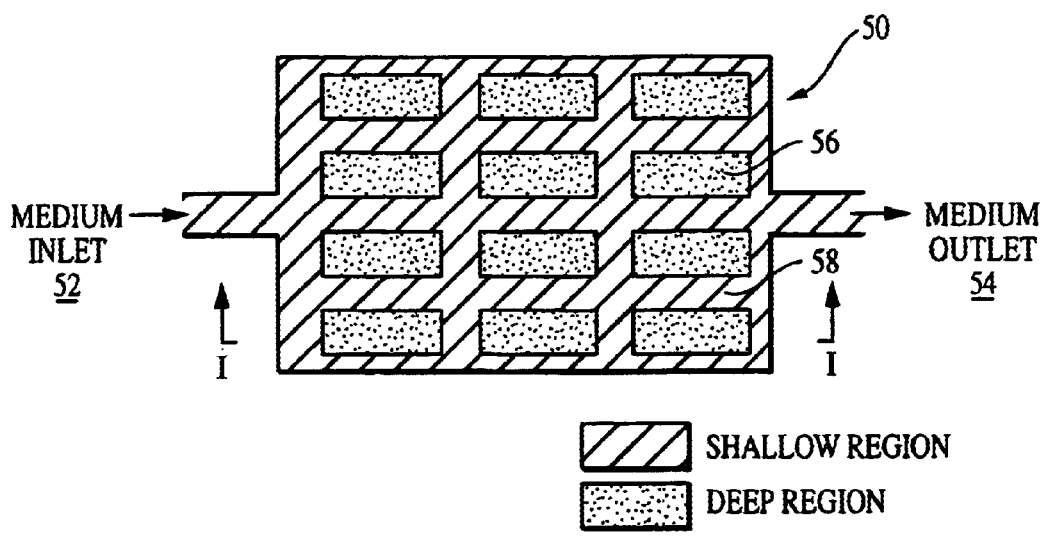
FIGS. 6(a)–6(b) illustrate a preferred culturing device constructed in accordance with the present invention.
Figure 6B:
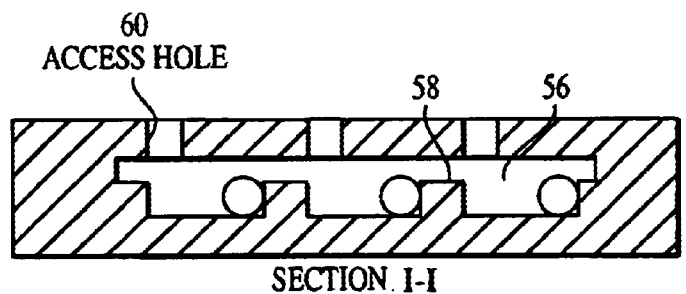

Referring now to FIGS. 6(a) and 6(b), an embryo culturing device 50 according to the present invention is shown. Fluid medium flow in the culture device 50 is in either direction between a medium inlet 52 and a medium outlet 54. The device includes a number of traps or compartments 56. As best seen in FIG. 6(b), the traps 56 comprise deep regions separated by shallow regions 58. Fluid flow between inlet 52 and outlet 54 is over shallow regions and through deep regions to move embryos back and forth within the deep region compartments 56. Embryos are inserted and removed through access holes 60, which may be formed by any of the preferred methods in FIGS. 5(a) through 5(c). In the device 50, artisans will thus appreciate that embryos may be moved back and forth within compartments 56 to simulate biological rotating, may experience the same medium conditions as other embryos within the culture, and may be easily removed and inserted. Though FIGS. 6(a) and 6(b) show a top loading embodiment for placing embryos within the compartment, the device will also work in a bottom loading arrangement, essentially inverted from that shown in FIGS. 6(a) and 6(b). In such a bottom loading arrangement, the embryos will still be held in the deep portions but cannot pass the shallow portions. An alternate embodiment might comprise a gap in place of shallow constrictions where embryos cannot pass through the gaps but fluid flow may occur therebetween and the depth of the gaps may be the same as those of the embryo holding compartments.

Figure 3A:
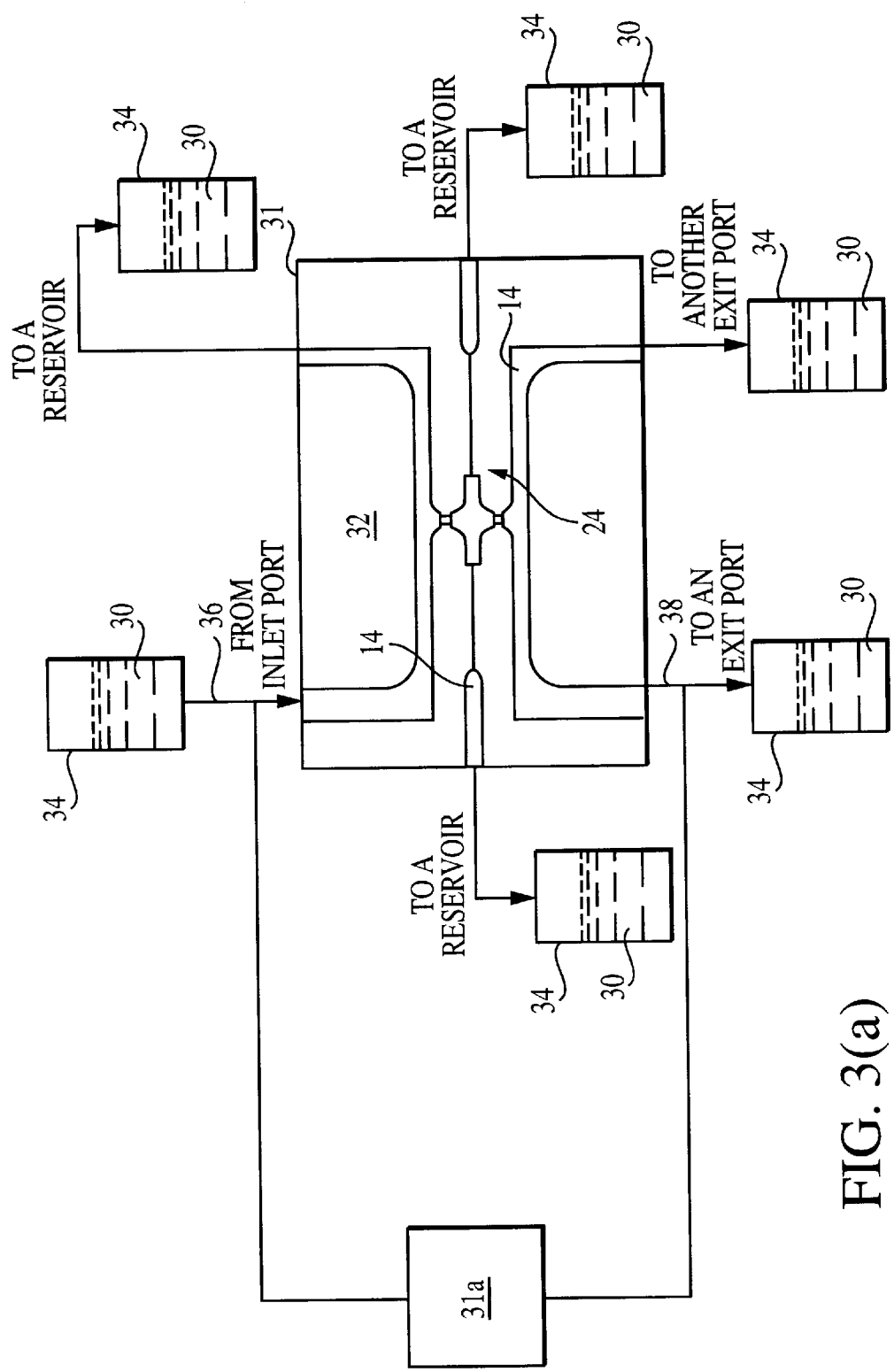
FIG. 3(a) is a perspective view of a preferred gravity flow driven microfluidic culturing and testing device constructed in accordance with the present invention.

Prototype devices like that shown in FIG. 3(a) have been produced and tested. Typical prototypes are described here for the sake of completeness. Artisans will appreciate that the manner of fabricating the prototypes may be accomplished by any other convention micro fabrication techniques. Artisans will also appreciate that production device manufacturing may differ significantly, and that specific numerical dimensions and conditions of the prototype devices do not limit the invention in the breadth described above.

In typical prototype channels, a pressure gradient of 1 Pa/mm causes the medium to flow on the order of $10^{-10}$ m$^3$/s (100 nl/s), with an average speed of 1 to 2 mm/s. Under these flow conditions the embryos roll along the bottoms of the channels; traveling at speeds ranging from ⅓ to ½ that of the fluid that would otherwise be in the same region of the channel. By manipulating the pressure at the wells connected to the ends of the channels, the embryos can be transported to (and retained at) specific locations including culture compartments and retrieval wells. Embryos fill a considerable portion of the channel, thereby greatly altering the flow of medium. The flow of medium through the channels is laminar.

Networks of prototype microfluidic channels have been fabricated in a device like that shown in FIG. 3(a) by etching trenches in 3-inch <100> silicon wafers, and then bonding glass covers to form channels. Devices including microfluidic channels have also been made by micromolding techniques in elastomers. Other plastics and techniques are also likely to be suitable, including, for example, injection molding of thermoplastic materials. Typical channel networks contain several branch microfluidic channels that intersect near the center of the device. The branches, which range from 1.5 to 2.5 cm in length, are 160 to 200 μm deep and 250 to 350 μm wide at the top. A first step in producing prototype devices involves patterning silicon nitride (SiN) coatings on using conventional photolithography techniques. The microfluidic channels are anisotropically etched with a potassium hydroxide (KOH) solution. Access holes in the glass covers are drilled, either conventionally using carbide tipped bits or ultrasonically. Glass covers are bonded to the wafers using UV curable epoxy (NOA 61, Norland Products, Inc, New Brunswick, N.J.) or Pyrex 7740 covers are anodically bonded to the wafers using 500V in a 450° C. environment. The nitride coatings are removed using buffered oxide etchant (BOE) before anodic bonding. Glass wells are bonded to the glass cover at the end of each branch of the channel network with either an epoxy (Quick Stick 5 Minute Epoxy or 5 Hour Set Epoxy Glue; both from GC Electronics, Rockford, Ill.) or a silicone adhesive (RTV 108 and RTV 118 from General Electric Co., Waterford, N.Y., or Sylgard® Brand 184, Dow Corning Corp., Midland, Mich.).

In the prototype devices, constrictions like those in both of FIGS. 2(a) ("narrow") and 2(b) ("shallow") have also been fabricated and tested. Channels with "narrow" constrictions, as shown in FIG. 2(a), can be fabricated using a single mask and etching operation. Channels with the "shallow" constrictions, as shown in FIG. 2(b), require two masks and two etching operations.

All the component materials of the prototype devices except the five minute epoxy were tested for embryo biocompatibility. In applying the present invention, artisans will appreciate that alternate materials may be used from those selected for the prototype devices, but biocompatibility must always be established through prior data and/or testing. Although many materials are known to be compatible with or toxic to certain cells, little work has been done to investigate the compatibility of materials used in micro fabrication with embryos. The materials selected may also vary depending upon the type of mammal from which the specific embryos to be handled are taken.

In prototype testing, two-cell mouse embryos (B6SJL/F2) were randomly assigned to and cultured on the substrata, in medium M16 (Sigma, St. Louis, Mo.) with bovine serum albumin (BSA; 4 mg/ml; Sigma), covered with mineral oil (Sigma). All embryos were cultured at 37° C. in a 5% $CO_2$ in air atmosphere for 96 h. Developmental rates of embryos were examined every 24 h. The percentage of embryos that reached the blastocyst stage for each material was compared with the percentage from the control group. Mouse embryos that reach the blastocyst stage, the latest possible stage before embryo transfer, are probably not developmentally hindered. While the absence of negative effects is not guaranteed unless the embryos are also transferred to recipient mice and monitored until the offspring are born, tests are commonly concluded at the blastocyst stage for practical and economic reasons. Most of the materials tested proved to be compatible with the mouse embryos, including silicon wafers, SiN coatings, NOA 61, and RTV 118. Some materials, such as the 5-minute epoxy, have not been tested since it is only used in conceptual devices to demonstrate mechanical and fluid principals of the invention, and would likely not be used in production devices.

Tests were run to examine several aspects of the prototype devices. Different tests required devices with different channel configurations. In all the tests, a halogen bulb via optical fibers illuminated the channel, which was viewed under a stereomicroscope. A graduated cylinder and a stopwatch were used to determine flow rates. Since the fluid is incompressible, the average fluid velocity in any section of channel is just the flow rate divided by the cross-sectional area.

Measurements of the rate of travel of the embryo for a given flow rate occurred in a simple straight channel, 29 mm long, 162 $\mu$m deep, and 160–380 (bottom-top) $\mu$m wide. The pressure gradient was varied and the speed of the embryo was measured for each setting. The channels were filled with phosphate buffered saline (PBS), with and without BSA. Flasks of the medium were connected to the channel. By adjusting the heights of the flasks, using micrometer head translation stages, the pressure difference was finely tuned to within 0.05 Pa. The flasks were connected to each other by tubing between the tests to zero the pressure head. The microfabricated prototype devices were cleaned in a hydrogen peroxide/ammonium hydroxide/deionized water solution and new pipet tips were adhered with epoxy before the tests were conducted. All the tests using PBS without BSA were conducted before those with BSA. Once the channels were filled with medium the mouse embryos were placed in the inlet well, at the channel entrance.

Tests were run to observe the influence of channel size and shape on the transport of embryos. For these tests, a device was fabricated with one long, circuitous channel with 11 sections each at one of four depths: 140, 164, 194, and 210 $\mu$m. At each depth the channel has 2 or 3 different widths. Widths, measured at the surface of the wafer, range from 275 to 480 $\mu$m. In the narrowest segments, the embryos were geometrically constrained to travel on a V-groove while in the other regions along a flat-bottomed channel. The speed of travel and rotating characteristics were observed and compared for different segments.

Observations of embryos at constrictions occurred in several devices, with both narrow and shallow type constrictions. Embryos were actually directed to specific constrictions. Altering the height of the medium in each well, by adding or subtracting fluid, tailored the pressure gradients in each branch of the channel network. Pressure heads were adjusted by a 1 to 8 mm (10 to 80 Pa).

Just as embryos placed in medium sink to the bottom of the container, embryos placed in microfluidic channels settle to the bottom. In all the tests, when the medium flowed, the embryos rolled and slid along the bottom of the channel in the direction of flow. Often they also remained in contact with one of the side walls of the channel. In initial tests without any surfactant in the medium (phosphate buffered saline) the embryos appeared to roll without slipping along the bottoms of the channels. Embryos slid or rolled with slip along the bottoms in later tests when the medium contained BSA (4 mg/ml).

Tests revealed that the rate of travel of an embryo in a channel depends upon the velocity of the medium. Sometimes they stick to the bottom of the channel when the velocity of the fluid around them is below 50 $\mu$m/s. For both media, PBS and PBS/BSA, a pressure gradient of 0.16 Pa/mm drives the flow through the channel at an average velocity of approximately 380 $\mu$m/s. The embryos roll at 187–250 $\mu$m/s, 49 to 66% of 380 $\mu$m/s. As the medium flows more quickly, the embryos roll faster, slipping as they roll. The actual speed of travel and the tendency to stick varies from one embryo to the next One embryo has been observed to travel 25% quicker than another at the same time in the same channel, in almost the same path line. In the observed range, 150 to 1000 $\mu$m/s, the velocity is linear with pressure gradient.

Results from testing the effects of channel size and shape match a priori predictions. For a given flow rate, the average fluid velocity and embryo speed is greater in a channel with smaller cross-sectional area. In contrast, for a given pressure gradient, the average fluid velocity and embryo speed is greater in a channel with larger cross-sectional area. In both cases, embryos travel slower on V-grooves than on flat-bottomed channels. Embryos are also more likely to become wedged and stuck in a V-groove than on a flat-bottomed channel.

Fluid under electroosmotic flow also caused embryos to roll through channels. An embryo rolled along the channel bottom at approximately 10 $\mu$m/s due to the pressure driven trickle flow. Switching on the voltage caused the mouse embryo to roll along the channel bottom 20 $\mu$m/s faster, at approximately 30 $\mu$m/s, toward the well with the negative electrode. With the voltage polarity reversed, the embryo rolled at approximately 10 $\mu$m/s in the reverse direction. No surfactant, such as BSA was used so there was little or no slipping. Electrical assistance, if used to move embryos, must be applied under carefully controlled conditions to avoid undesirable heating of the medium.

Computational fluid dynamics modeling using Fluent/UNS 4.2 (Fluent, Inc., Lebanon, N.H.) and 2-dimensional finite element analysis of prototype microfluidic channels with constant cross-section using Quickfield (Tera Analysis, Inc., Tarzana, Calif.) verified the observed flow rates and flow patterns. The embryo was modeled as a rigid sphere.

Recall that the embryo does not appear to deform under typical conditions. To analyze the laminar flow, 1 or 2 mm sections of channel were meshed into 10,000 to 30,000 tetragonal elements. Once verified, computer modeling was used to determine flow velocity profiles, design constrictions with lower pressure drops, to observe forces on embryos retained at constrictions, and to analyze electrically driven flows in similar channels. However, analysis incorporating adhesion of the embryo to the channel walls and distortion of the embryo would be significantly more complex and was not attempted.

As discussed above, in the straight channel tests of embryo velocity, the medium had an average velocity of 380 $\mu$m/s under a pressure gradient of 0.16 Pa/mm. Finite element analyses determined the centerline velocity to be 815 $\mu$m/s under these conditions. When traveling in the channel, the embryo was tangent to the bottom and one wall. Consider a 100 $\mu$m diameter circle tangent to the bottom and one side of the channel. The average velocity of the fluid traveling through this circle when the embryo is not present is 480 $\mu$m/s. However, the embryos rolled at only 187–250 $\mu$m/s, 39–52% as quickly, in both PBS and PBS/BSA media. The velocity profile encourages the embryo to roll forward and along the wall, which confirms visual observations. In sum, embryos roll at $\frac{1}{3}$ to $\frac{1}{2}$ the speed at which fluid would flow in the same region of the cross section.

The constrictions greatly increase fluid resistance in the channels. Standard analytical formulas can help approximate the resistance, but the cross-sectional shapes of the constrictions vary with position. Three-dimensional models of the constrictions were analyzed before masks were designed and wafers were etched. The information gained from the finite element analyses led to optimally-sized constrictions. The shallow constrictions, sized individually for the geometry of the device, balance the need for minimal flow resistance and robust fabrication. Typical constrictions have a minimal depth of 20 $\mu$m.

Studies of the placement of the embryos at the traps reveal lateral forces on the order of $10^{-8}$ to $10^{-7}$ N force the embryo to the side and part way up the ramp at the entrance to the shallow constriction.

The tests revealed several interesting characteristics of microfluidic transport, such as variations in velocity between embryos and the tendency to roll along the bottoms of the channels, often tangent to a side wall. However, the testing did reveal several other issues. Electroosmotic flow may be useful to assist embryo movement, and more so for movement of plugs of material useful in embryo treatment and fertilization techniques. Electrical control of fluid flow must be carefully controlled since high voltages may harm the embryos in several ways. Even with the embryos in sections of channel away from the electric fields, the applied energy heatsup the medium (Joule heating) beyond physiological temperatures and the electrolysis products alter the pH. Note that an embryo requires about 0.029 Osmol, i.e., a relatively high conductivity. Also, EOF is degraded in channels with surfactant, but the embryos survive better in medium with a surfactant, such as BSA.

Microfluidic transport free of electrical assistance offered through gravity fed devices like that in FIG. 3(a), or through pumped fluid pressure devices, offers an important advantage. The medium can be easily altered with time to meet the changing requirements of the developing embryos. Gradually changing the composition of the medium avoids inducing stresses upon the embryo from the abrupt environmental changes that often accompany transfer from one petri dish to a second dish with a different medium. The microfluidic handling of embryos by the invention is not physically harsher than transfer with pipets and definitely less damaging than many techniques in conventional practice including some which pierce the outer membrane.

It is anticipated that control of fluid flow, and therefore embryo positioning, in handling devices like that shown in FIG. 3(a) will be handled through programmed control instruments for largely automated devices. Alarms and warnings may be incorporated based upon sensed conditions within an embryo handling device of the invention. In similar fashion, monitoring of embryos with conventional instruments applied to a handling device of the present invention. Artisans will generally recognize that the microfluidic embryo handling device thus forms a basic building block upon which many useful devices may be based, and that such devices will incorporate the essence of the present invention.

Some particular devices have been demonstrate for manipulation, testing and handling of embryos and oocytes. A particular geometry of microfluidic channels is shown in FIGS. 7(a) and 7(b), and has been demonstrated to enable cumulus removal from oocytes. The geometry is a series of gradually more constricted sections of microfluidic channels, best seen in FIG. 7(a). Though FIG. 7(a) shows curved constricted sections, the constricted need not be curved. Inner surfaces of the constricted sections preferably have protrusions in the form of teeth or serrations to aid cutting of the cumulus as it passes. The last section in a series has protrusions separated at a distance apart to avoid damage to the oocyte, with the preceeding sections having protrusions spaced at gradually smaller distances apart to cut portions of surrounding cumulus as fluid pressure forces the oocyte through a constricted section. In FIG. 7(a), multiple constricted sections each individually have protrusions with equal spacing, with a downstream section from a previous section using a lesser spacing. One could also construct a single section in which protrusions within the section gradually become closer together to accomplish the same purpose of cutting deeper into the cumulus at multiple locations without damaging the embryo. The FIGS. 7(a) and 7(b) geometry has been used to remove cumulus from cattle oocytes. In a prototype device, straight sections of microfluidic channel were 500 microns wide. Five constricted sections were used. The first and largest section included protrusions spaced at 300 microns gradually decreasing to the fifth constricted section that was 50 microns wide. The first four constrictions cut (a "mohawk" cut has been observed) the cumulus as the cumulus-oocyte complex passes, forced along by fluid flow. At the fifth constriction half of the cumulus was suctioned off. Flow was reversed a few times to reposition the oocyte until the other half of the cumulus was drawn through the final constriction. Thus, appropriately dimensioned constrictions and geometry may be used to position and condition an embryo and surrounding structure.

Figure 8A:
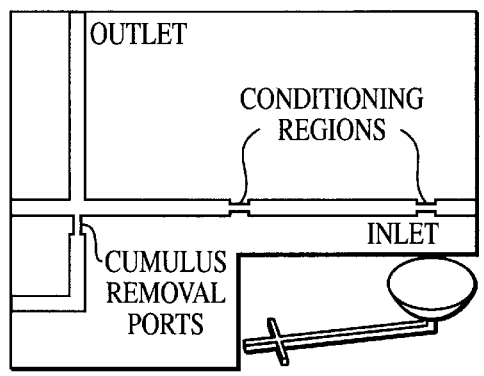
FIGS. 8(a) and 8(b) illustrate a complete prototype device for cumulus removal.
Figure 8B:
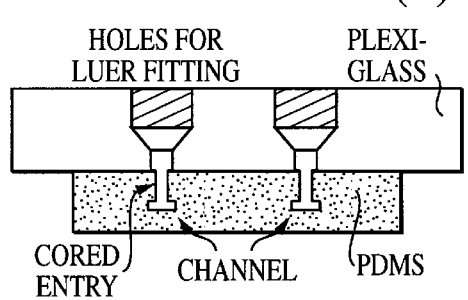
Figure 8C:
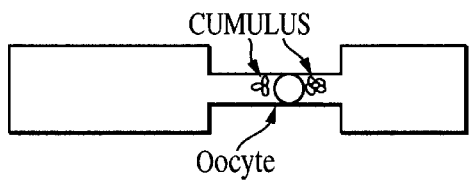
FIGS. 8(c)–(f) illustrate steps used in experiments with the FIGS. 8(a) and 8(b) prototype to remove cumulus from an oocyte.
Figure 8D:
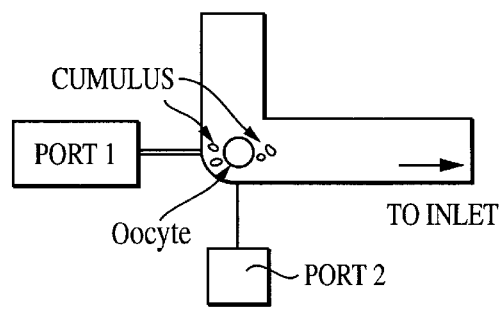
Figure 8E:
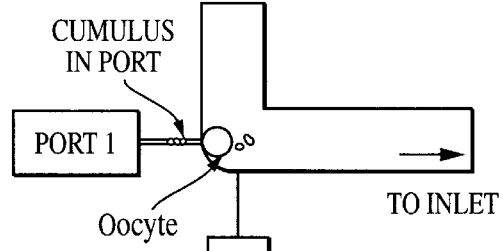
Figure 8F:
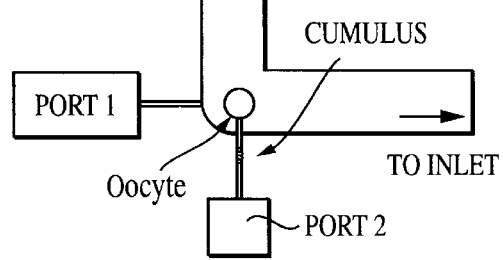

A complete prototype device for cumulus removal is depicted in FIGS. 8(a) and (b), while FIGS. 8(c)–(f) illustrate steps used in experiments with the FIGS. 8(a) and 8(b) prototype to remove cumulus from an oocyte. A polypropylene well is bonded to a loading port to provide a larger fluid reservoir at the inlet shown in FIG. 8(a). An acrylic syringe connection module exit ports so that standard syringes or other fittings can be connected to the device. Syringes enable manual pressure control, or a syringe pump can serve as a precise flow controller the plexi-glass and PDMS prototypes allowed for embryo positioning throughout a channel network and parking of the oocyte at desired locations during testing. In addition, the prototype devices provide complete optical access (important for embryo analysis), rapid prototyping, and easy integration with future analysis sensors. Loading oocytes in the device is simplified through the use of a funnel-shaped inlet well (inset in FIG. 8(b)). The funnel shape is molded at the entrance to the channel with the tip of the funnel connected to the head of the channel. This wide funnel configuration allows an oocyte complex to be easily inserted. Oocytes will typically sink to the funnel bottom. The sloped walls guide the complex into the channel entrance at the bottom of the funnel. This method of loading simplifies the handling procedures because it does not require precise lateral positioning. To manipulate the cumulus cells into a configuration that allows for complete cumulus removal, the complex is passed through two constricted regions (FIG. 8(c)). These narrowed regions force the cumulus into two main clumps at the front and back of the oocyte, as shown in FIG. 8(d). The two constricted cumulus conditioning regions (FIG. 8(a) were 200 and 150 µm wide, respectively. The cumulus gets damaged and bunched in the conditioning regions and then flows to removal ports (see FIGS. 8(d)–8(f)), which comprised two thin channels placed ninety degrees from one another at a bend in the microfluidic channel in the prototype device. The ports allow the cumulus to enter (FIGS. 8(e) and 8(f)) while being too small for an oocyte. Using fluid flow control, cumulus is suctioned off the oocyte, first trough one port and then the other.

Microfluidic channels of the invention have also been used to realize novel methods of embryo health evaluation, by analysis of mechanical properties of the embryos. Specific mechanical properties demonstrated to distinguish health embryos include surface properties and deformation properties of embryos. The tendency of an embryo to return its shape after being deformed to a point short of permanent damage is believed to be an indicator of health because embryos actively maintain their shape. Embryos selectively transport ions through their membranes and the proteins of the zona pellucida are constantly reorienting themselves to resist external forces. Transport of ions and other substrates/metabolites into and out of the embryonic cells is a function of the health of the embryo. Unhealthy embryos have degraded ability to transport ions, and a corresponding degraded ability to return their shape after being deformed to a point that avoids permanent damage. The control of pressure and the ability to position embryos at constrictions offers the opportunity to deform embryos with a control that prevents permanent deformation of health embryos. Deformation testing has been conducted keeping pressure gradients below 0.1 Pa/m (1 mm water/cm) and fluid velocities at or below a few millimeters per second.

FIGS. 9(a)–9(d) illustrate a deformation evaluation of an embryo used as an indicator of embryo viability. A constriction is sized to cause deformation of an embryo as it passes through due to fluid pressure. A healthy embryo better returns its shape in FIG. 9(d) after having passed through the constriction. Alternatively, an embryo might be deformed at constriction sized to prevent passage. After for a period of deformation at a constriction, flow is reversed, reversed and stopped, or stopped, allowing the embryo to return its shape.

The precise control of pressure offered by microfluidic channels also permits evaluation of embryo stiction to channel walls, as healthy embryos will stick more. Thus, a healthy embryo can quantitatively be measured to travel more slowly down a channel as compared to an unhealthy embryo. Alternatively, distance of travel can be similarly compared, with a healthy embryo traveling a shorter distance under identical flow and pressure conditions.

Fluid analysis of embryos is better enabled by devices incorporating microfluidic channels of the invention. Fluid is collected from a downstream channel of a microfluidic channel culturing device of the invention. In accordance with devices formed according to the invention, the collected fluid will have flowed past an embryo since devices of the invention avoid stagnant conditions and sizing of the microfluidic channels causes fluid in the channels to pass close to an embryo. When downstream fluid is collected, it may be desirable to add a similar amount of upstream fluid to maintain pressures and flows within a microfluidic device from which fluid samples are being collected. An exemplary channel configuration for fluid collection is shown in FIG. 10. An embryo 16 is positioned at a mechanical constriction. Downstream, a collection or analysis cell 70 provides fluid which has passed in close proximity to the positioned embryo. A side channel 72 may provide a second fluid to aid analysis, which may be mixed in with a main flow with the assistance of peg formations 74, though mixing is achieved without formations as shown in previous figures. Programmable syringe pumps can be used for removal of fluid samples and insertion of additional upstream fluid. Alternatively, all of fluid downstream an embryo could be collected. This fluid is then analyzed, such as by chemical or optical analysis.

Systems of the invention can be used for complete oocyte maturation, fertilization and embryo culturing without harsh manipulation techniques. The ability to control fluid and position embryos offers the chance to mature an oocyte, bring sperm or seminal fluid into contact, and then simulate biological embryo culturing, all within a single device of the invention. Maturation (IVM), fertilization (IVF) and culturing (EC) require different media, sperm capacitation and rinsing procedures. Systems of the invention using microfluidic channels allow rapid change and precise control of such conditions, allowing changing of the composition of the fluidic medium over the course of hours or days to simulate secretion and growth factor accumulation in the female reproductive tract and embryo movement to different parts of the tract. Medium can be controlled to flow slowly past each embryo (or oocyte) to provide a fresh supply of nutrients. Periodic flows, e.g. once an hour, as opposed to continuous flows, would allow a limited build-up of beneficial autocrine and paracrine factors without allowing waste products to accumulate. All of the current IMF, IVF and EC techniques can be performed in a single device of the invention such that a given oocyte-embryo does not have to be handled or moved during a sequential IMF, IVF and EC procedure or during any one of the individual procedures.

Systems of the invention may reduce rates of polyspermy, use smaller numbers of spermatozoa, and incorporate a swim-up technique to select the most motile sperm. In typical human IVF procedures, the egg is surrounded by 50,000 to 100,000 sperm in a 0.5 to 1.0 ml drop of medium. This number could be reduced since the microfluidic channels provide a flow control to bring sperm and oocyte together.

In livestock IVF, rates of polyspermy are high, about 40–70% in pigs, for example. According to the invention, microfluidic channels cause sperm to pass very close to oocytes, e.g., about 30 µm. In addition, the time interval in which the sperm are near the oocyte can be controlled by controlling the rate of media flow. Alternatively, a parked oocyte positioned according to the invention can be held very close to the point of insertion of a comparatively small fluid packet of sperm, providing a high concentration of sperm near the oocyte while reducing the chance of polyspermy. Discrete plugs or boluses may deliver one to a few sperm to create a situation analogous to the situation in vivo in the oviduct where there are few numbers of sperm at any one time. This ability, with a T-junction or other physical or effective constriction to position an embryo, allows for delivery of one to a few sperm to the proximity of the ovum to reduce the chance of polyspermy. In addition, channel geometry being embryo scaled allows for increased contact between the ovum and the sperm. Sperm and "bounce" off the side walls and increase the effecfive contact between the sperm and the egg.

Cryopreservation is another technique that would benefit from the ability to position embryos according to the invention, and the ability to precisely control the fluid environment around the embryo. Cryopreservatives may be delivered to a positioned or moving embryo in a device of the invention, which can then later be used to reverse the cryopreservation process. Change of the fluid can then be used to conduct maturation, fertilization, and culturing, as described above.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

What is claimed is:

1. A method for evaluating embryos, the method comprising steps of:
   placing an embryo in an approximately embryo scaled fluid channel;
   creating a fluid flow in the fluid channel; and
   evaluating an embryo characteristic while an embryo is within the embryo scaled fluid channel.

2. The method according to claim 1, wherein said step of creating a fluid flow moves an embryo in the fluid channel, and said step of evaluating an embryo characteristic comprises measuring the speed at which an embryo moves in the fluid channel.

3. The method according to claim 1, wherein said step of creating a fluid flow moves an embryo in the fluid channel, and said step of evaluating an embryo characteristic comprises measuring the distance an embryo moves in the fluid channel.

4. The method according to claim 1, wherein said step of evaluating comprises obtaining a fluid sample from the fluid channel downstream of an embryo in the fluid channel and conducting a chemical analysis of the fluid sample.

5. The method according to claim 1, wherein the fluid channel includes a constriction sized to deform an embryo as it passes through and said step of evaluating evaluates a tendency of an embryo to return its shape after passing through the constriction.

6. The method according to claim 1, wherein the fluid channel includes a constriction sized to prevent passage of an embryo, said step of creating creates a fluid flow to move an embryo to the constriction and then deform it slightly by fluid pressure for a short period of time, and said step of evaluating evaluates a tendency of an embryo to return its shape after being deformed for the short period of time.

7. A method for treating embryos, the method comprising steps of:
   placing an embryo in an approximately embryo scaled fluid channel;
   creating a fluid flow in the fluid channel; and
   treating an embryo to alter a characteristic of the embryo while it is positioned within the fluid channel.

8. The method according to claim 7, wherein said fluid channel includes a series of constrictions including protrusions having gradually less space therebetween, and said step of treating comprises manipulating the fluid flow in the fluid channel to pass an embryo through one or more of the constrictions and to remove cumulus.

9. The method according to claim 8, wherein a last one of the series of constrictions is sized to block passage of the embryo, and said step of treating comprises manipulating the fluid flow in the fluid channel to pass an embryo through other ones of the series of constrictions and then manipulating the fluid flow to suck off cumulus when an embryo is positioned at the last one of the series of constrictions.

10. The method according to claim 7, wherein the fluid channel includes a constriction sized to prevent passage of an embryo, said step of treating comprises altering the fluid in the fluid channel to pass an acidic solution over an embryo positioned at the constriction to remove zona pellucida.

11. A microfluidic embryo handling device comprising:
   an embryo transport network having a biological medium for movement of embryos inserted therein, said transport network including an approximate embryo scaled embryo fluid channel and an opening for delivering fluid into the transport network; and
   a t-junction in the transport formed at the intersection of two fluid channels, and a second opening for delivering fluid into the transport network at a separate fluid channel location.

12. The device according to claim 11, further comprising a well in said fluid channel formed to hold an embryo during periods predetermined flow rate within said fluid channel and allow escape of an embryo during periods of lower than said predetermined flow a rate within said fluid channel.

13. A microfluidic embryo fertilization device comprising:
   an embryo transport network having a biological medium for movement of embryos inserted therein, said transport network including an approximate embryo scaled embryo fluid channel and an opening for delivering fluid into the transport network; and
   a T-junction in the transport network formed at the intersection of two fluid channels, and a second opening for delivering sperm into the transport network at a separate fluid channel location.

* * * * *

UNITED STATES PATENT AND TRADEMARK OFFICE
CERTIFICATE OF CORRECTION

PATENT NO. : 6,695,765 B1
DATED : February 24, 2004
INVENTOR(S) : Beebe et al.

It is certified that error appears in the above-identified patent and that said Letters Patent is hereby corrected as shown below:

Column 18,
Line 48, after "flow" delete "a".

Signed and Sealed this

Fifth Day of October, 2004

JON W. DUDAS
*Director of the United States Patent and Trademark Office*